United States Patent
Satou et al.

(10) Patent No.: US 8,360,996 B2
(45) Date of Patent: Jan. 29, 2013

(54) GUIDE WIRE

(75) Inventors: Hideo Satou, Fujinomiya (JP); Hideki Fujimagari, Irvine, CA (US); Fumihiko Mouri, Fujinomiya (JP)

(73) Assignee: Terumo Kabushiki Kaisha, Shibuya-ku, Tokyo (JP)

( * ) Notice: Subject to any disclaimer, the term of this patent is extended or adjusted under 35 U.S.C. 154(b) by 0 days.

(21) Appl. No.: 12/933,249

(22) PCT Filed: Mar. 17, 2009

(86) PCT No.: PCT/JP2009/055184
§ 371 (c)(1),
(2), (4) Date: Sep. 17, 2010

(87) PCT Pub. No.: WO2009/119386
PCT Pub. Date: Oct. 1, 2009

(65) Prior Publication Data
US 2011/0015618 A1    Jan. 20, 2011

(30) Foreign Application Priority Data
Mar. 27, 2008 (JP) .................. 2008-085015

(51) Int. Cl.
*A61M 25/00* (2006.01)
(52) U.S. Cl. .................................... 600/585
(58) Field of Classification Search .......... 600/433, 600/434, 585; 604/164.13
See application file for complete search history.

(56) References Cited

U.S. PATENT DOCUMENTS

| | | | |
|---|---|---|---|
| 5,069,226 A | | 12/1991 | Yamauchi et al. |
| 5,377,690 A | * | 1/1995 | Berthiaume ................. 600/585 |
| 5,411,476 A | | 5/1995 | Abrams et al. |
| 5,520,194 A | * | 5/1996 | Miyata et al. ............... 600/585 |
| 5,551,444 A | * | 9/1996 | Finlayson .................... 600/585 |
| 5,724,989 A | * | 3/1998 | Dobson ....................... 600/585 |

(Continued)

FOREIGN PATENT DOCUMENTS

| | | |
|---|---|---|
| JP | 2-289267 A | 11/1990 |
| JP | 4-292174 A | 10/1992 |

(Continued)

OTHER PUBLICATIONS

International Search Report (PCT/ISA/210) issued on Apr. 14, 2009, by Japanese Patent Office as the International Searching Authority for International Application No. PCT/JP2009/055184.

*Primary Examiner* — Max Hindenburg
*Assistant Examiner* — Jonathan M Foreman
(74) *Attorney, Agent, or Firm* — Buchanan Ingersoll & Rooney PC (57) ABSTRACT

A guide wire for a catheter is inserted for use into the catheter and has a wire body, a reshapeable shaping ribbon (wire material) mounted such that a part of the base end side of the shaping ribbon is fixed to the front end side (small diameter section) of the wire body and a part of the front end side of the shaping ribbon extends in the direction to the front end of the guide wire from the front end of the wire body, and a helical coil installed so as to cover both the front end side of the wire body and the shaping ribbon. The coil is divided into a first coil and a second coil, and the first coil is divided into a fine pitch section and a rough pitch section. The bending rigidity of the fine pitch section is greater than that of the rough pitch section.

16 Claims, 5 Drawing Sheets

U.S. PATENT DOCUMENTS

| | | |
|---|---|---|
| 5,865,767 A | 2/1999 | Frechette et al. |
| 6,390,992 B1 * | 5/2002 | Morris et al. ................. 600/585 |
| 7,951,094 B2 * | 5/2011 | Johansen et al. ............. 600/585 |
| 2004/0167442 A1 | 8/2004 | Shireman et al. |
| 2004/0167443 A1 | 8/2004 | Shireman et al. |
| 2006/0235337 A1 * | 10/2006 | Vrba et al. .................... 600/585 |
| 2007/0123805 A1 * | 5/2007 | Shireman et al. ............. 600/585 |

FOREIGN PATENT DOCUMENTS

| | | |
|---|---|---|
| JP | 6-054912 A | 3/1994 |
| JP | 10-309319 A | 11/1998 |
| JP | 2006-519068 A | 8/2006 |
| JP | 2007-135645 A | 6/2007 |

\* cited by examiner

GUIDE WIRE

TECHNICAL FIELD

The present invention relates generally to guide wires and in particular to a guide wire used to introduce a catheter into a body cavity such as a blood vessel or a bile duct.

BACKGROUND ART

In the past, a catheter has been introduced into a blood vessel in order to examine or cure a heart disease or the like. To introduce such a catheter to a target site in a body, a guide wire is inserted into the catheter and a distal end of the guide wire is allowed to go ahead. The distal end of the guide wire is allowed to reach the target site and thereafter the catheter is guided to the target site.

In particular, in PCI (Percutaneous Coronary Intervention), while selecting a branch of a coronary artery under radiographic guidance, the distal end of the guide wire is allowed to reach a vascular narrowing portion as a target site and passed through it. Thereafter, an expansion catheter equipped with a balloon at a distal end is inserted along the guide wire and the balloon of the expansion catheter is located at the vascular narrowing portion. The balloon is expanded to push and widen the vascular narrowing portion to ensure blood flow. In this way, a treatment for angina or the like can be performed.

In such an treatment, to insert the guide wire from a femoral artery and advance it to an aorta, an aortic arc and a coronary artery, the guide wire requires the following: flexibility and restoring performance for following the shape of a blood vessel, indentation performance and torque transmissibility (generically referred to as "operability") for reliably transmitting to a distal end force encountered when a proximal portion of the guide wire is pressed, anti-kink performance (anti-bending performance), etc.

To advance the guide wire from a branch portion of the coronary artery to a desired branch, shaping in which the distal end of the guide wire is shaped to conform to the shape of the branch portion is performed with fingers. Such work is called reshaping.

For example, if a guide wire is inserted into a peripheral side coronary artery, a conventional distal shape such as an angle-type or J-type preliminarily molded cannot select a desired branch. Because of this, the distal end of the guide wire is formed in advance into a desired shape for insertion in many cases. If such a shape still does not conform to the desired branch, the guide wire is once removed from the catheter and reshaped.

As the reshapeable guide wire, a guide wire is proposed that includes e.g. a superelastic core material; a reshaping member secured to the vicinity of the distal end of the core material; and a coil obtained by helically forming a raw-wire and installed to cover the distal end of the core material and the reshaping member. (See e.g. patent document 1.) In this guide wire, also the coil is secured to the vicinity of the distal end of the core material together with the reshaping member. The guide wire described above is such that the distal end can be reshaped by the function of the reshaping member.

The reshaping member disclosed in patent document 1 is formed rectangular in transverse section; therefore, it is called a shaping ribbon. This shaping ribbon is formed of a material tending to be plastically deformed, such as stainless steel or the like.

However, the guide wire provided with such a shaping ribbon has a large difference between the bendability (bending rigidity) of the superelastic core material and the bendability (bending rigidity) of the shaping ribbon, which results in that the joint portion between both causes stress resulting from the difference of the bendability (bending rigidity). If the stress concentrates, the shaping ribbon is bent in the vicinity of the joint portion so that the function as the guide wire is impaired.

The guide wire described in patent document 1 is provided with a coil obtained by helically forming a raw-wire. The raw-wire is different in pitch between both sides of the joint portion mentioned above. However, in the coil, the pitch of the raw-wire is rough on the distal end side of the joint portion but fine on the proximal end side thereof. Therefore, the difference in the pitch of the raw-wire in the coil described above acts to further increase the stress resulting from the difference in the bendability (bending rigidity) between the core material and the shaping ribbon described above.

Because of this, the guide wire described in patent document 1 has a concern that because of bending, the shaping ribbon does not sufficiently function in a bent blood vessel.

Patent Document 1: Japanese Patent Laid-open No. Hei 4-292174

DISCLOSURE OF INVENTION

It is an object of the present invention to provide a high reliable guide wire that alleviates stress concentration caused by a reshaping member and has excellent reshaping performance and operability.

To achieve the above object, the present invention is a guide wire including: a wire main body having flexibility; a reshapeable wire material having a portion, on a proximal end side, secured to a distal end side of the wire main body, and an extending portion, at a portion on a distal end side, extending in a distal direction from a distal end of the wire main body; and a coil installed to cover the distal end side of the wire man body and the wire material, the coil being obtained by helically forming a raw-wire; and characterized in that in the coil, bending rigidity of the coil per se of a distal end side portion located at a position corresponding to the extending portion is higher than that of a proximal end side portion located at a position closer to the proximal end side than to the distal end side portion.

According to the present invention described above, the bending rigidity of the distal end side portion of the coil per se is higher than that of the proximal end side portion. Therefore, the difference of the bending rigidity of the coil per se is used to suppress the local concentration of stress on the joint portion between the wire material and the wire main body. Thus, the wire material can be prevented from being bent. Consequently, there is no possibility that the guide wire cannot be used because of bending, and the guide wire has high reliability, combining excellent reshaping performance and operability.

Preferably, the difference in the bending rigidity of the coil results from a difference in the pitch of the raw-wire between the distal end side portion and the proximal end side portion.

With this, only the simple provision of the difference in the pitch of the raw-wire can easily alleviate the difference in the bending rigidity between the distal end side portion and proximal end side portion of the guide wire. This can enhance the reliability of the guide wire.

Preferably, the distal end side portion of the coil is obtained by multi-helically forming the raw-wire and the proximal end side portion of the coil is obtained by single- or multi-helically forming the raw-wire. In addition, a difference in the bending rigidity of the coil results from a difference in the overlapping number of the raw-wire between the distal end side portion and the proximal end side portion.

With this, only the simple provision of the difference in the overlapping number of the raw-wire can easily alleviate the bending rigidity between the distal end side portion and proximal end side portion of the guide wire. This can enhance the reliability of the guide wire.

Preferably, a difference in the bending rigidity of the coil results from a difference in hardness of the raw-wire per se between the distal end side portion and the proximal end side portion.

With this, by simply subjecting a portion of the coil to the treatment of forming a difference in the hardness of the raw-wire such as annealing, the difference in bending rigidity between the distal end side portion and proximal end side portion of the guide wire can easily be alleviated. Thus, the reliability of the guide wire can be enhanced.

Preferably, a difference in the hardness of the raw-wire per se results from a difference in the condition of annealing applied to the raw-wire between the distal end side portion and the proximal end side portion.

With this, by just partially varying the annealing applied to the coil, the difference in bending rigidity between the distal end side portion and proximal end side portion of the guide wire can easily be alleviated and thus the reliability of the guide wire can be enhanced.

Preferably, the bending rigidity of the coil per se in the distal end side portion is partially gradually reduced from the proximal end side toward the distal end side.

With this, also the bending rigidity of the entire guide wire can be reduced toward the distal direction without the abrupt difference in rigidity. Therefore, while preventing the bending of the wire material, particularly the flexibility of the most distal portion can be increased. Thus, when the guide is inserted into a blood vessel, insertion operation can be done safely without any damage to the wall of the blood vessel.

Preferably, the difference in the bending rigidity of the coil is set to complement the difference between the bending rigidity of the extending portion of the wire material and the bending rigidity of the portion where the wire material and the wire main body overlap each other.

This can reliably suppress the concentration of stress occurring at the joint portion between the wire material and the wire main body. Thus, the bending of the wire material can reliably be prevented.

If it is assumed that the bending rigidity of the portion of the guide wire corresponding to the distal end side portion is X and that of the portion corresponding to the proximal end side portion is Y, preferably X/Y is 0.7 to 1.

With this, the guide wire is entirely uniform in bending rigidity and is slightly soft on the distal end side. Therefore, the guide wire can easily be inserted into a blood vessel and is high in operability.

Preferably, the wire material is formed like a flat plate or rectangular column.

With this, since the transverse sectional shape of the wire material is a rectangle, the bending of the rectangle in the long-side direction is easier than that in the short-side direction. Therefore, there is an advantage that the directionality of reshaping of the wire material can be defined with ease. In addition, if such a wire material is compared with a wire material circular in transverse cross-section, although having the same cross-sectional shape and almost the same tensile strength, the wire material can ensure flexibility in the long-side direction. Therefore, following-deformability encountered when the wire material is subjected to stress can be enhanced.

Preferably, the length of the extending portion of the wire material is 0.5 to 1 time the portion other than the extending portion.

With this, the guide wire is superior in insertion property into a blood vessel and in selectability of a blood vessel branch.

Preferably, the length of the extending portion of the wire material is 5 to 20 mm.

With this, the guide wire is increased particularly in operability and consequently it has higher safety.

Preferably, the coil is secured to a portion where the wire material and the wire main body overlap each other.

This enhances the reliability of the guide wire.

Preferably, the wire material is secured to the wire main body at two positions, i.e., the distal portion and the proximal portion, of the portion where the wire material and the wire main body overlap each other.

With this, the wire material and the wire main body are partially secured to each other not entirely of the overlapping portion. Therefore, the mechanical characteristic of the overlapping portion becomes a characteristic combining the characteristic of the wire main body and the characteristic of the wire material. For this reason, if the a material exhibiting superelasticity such as a Ni—Ti alloy is used as the wire main body, the mechanical characteristic of the overlapping portion will combine the reshaping performance of the wire material and this super-elasticity. The guide wire having such a portion can easily be inserted into a blood vessel and is superior in selectability of a branch at a branch portion of the blood vessel (superior in operability).

BEST MODE FOR CARRYING OUT THE INVENTION

A guide wire of the present invention will hereinafter be described in detail according to preferred embodiments illustrated in the accompanying drawings.

First Embodiment

A description is first given of a first embodiment of the guide wire of the present invention.

Figure 1:
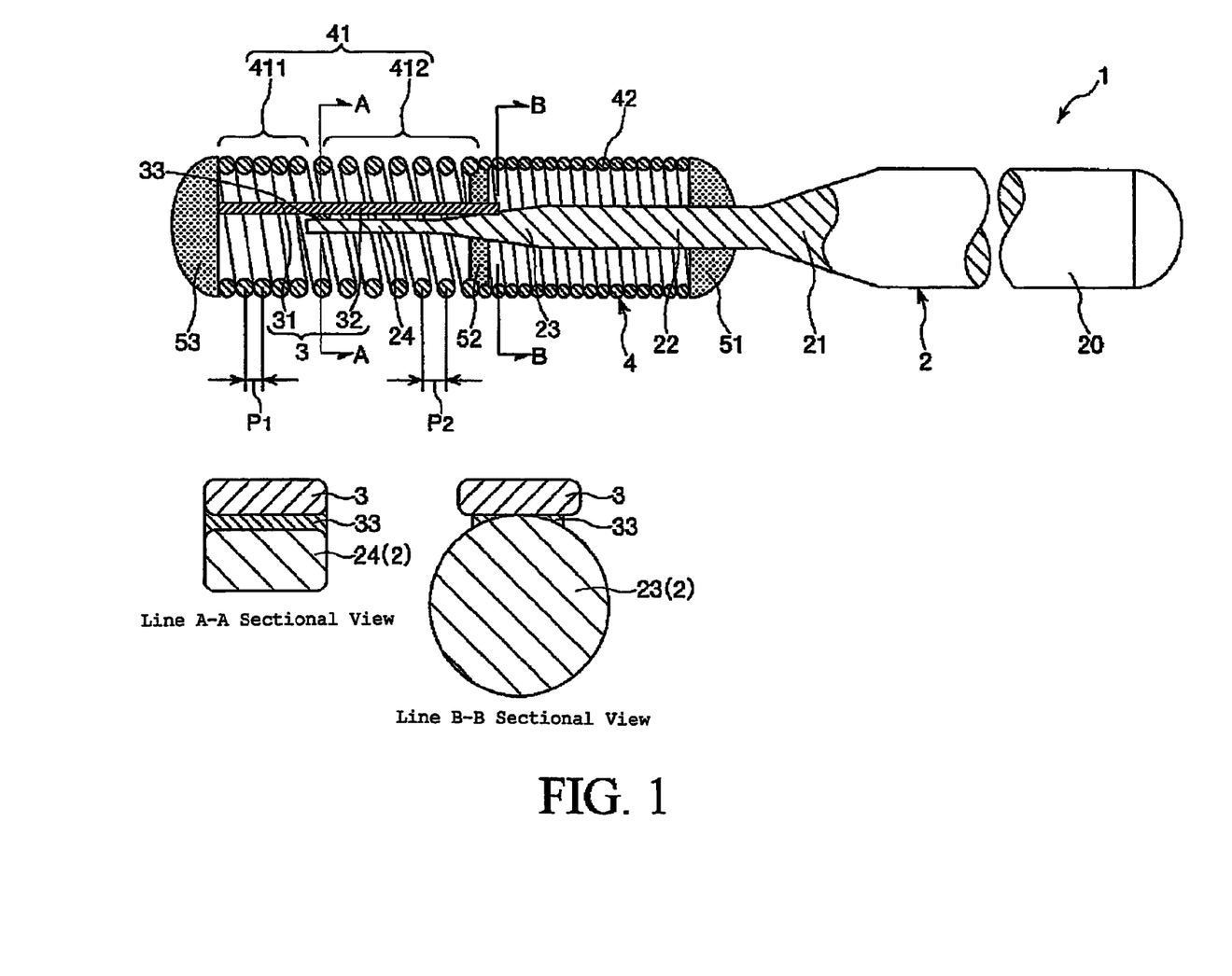
FIG. 1 is a longitudinal cross-sectional view illustrating a first embodiment of a guide wire of the present invention.

FIG. 1 is a longitudinal cross-sectional view illustrating a first embodiment of the guide wire of the present invention. It is to be noted that the right and left in FIG. 1 are referred to as "the proximal end" and "the distal end," respectively, for explanatory convenience. In addition, for easy understanding, FIG. 1 schematically illustrates the guide wire shortened in longitudinal length and exaggerated in diameter so that the ratio between the longitudinal length and the diameter is largely different from that between the actual ones.

The guide wire 1 illustrated in FIG. 1 is a guide wire for catheter inserted into the catheter for use. The guide wire 1 includes a wire main body (wire core) 2 mainly forming the guide wire 1; a reshapeable shaping ribbon (wire material) 3 installed such that a proximal end side portion is secured to the distal end side (a small-diameter portion 24) of the wire main body 2 and a distal end side portion extends in the distal direction from the distal end of the wire main body 2; and a helical coil 4 installed to cover the distal end side of the wire main body 2 and the shaping ribbon 3.

The wire main body 2 is preferably made of metal material and as illustrated in FIG. 1 includes a main body portion 20 relatively large in external diameter; a first tapered portion 21 and a second tapered portion 23 located on the distal end side of the main body portion 20 and gradually reduced in external diameter toward the distal direction; an intermediate portion 22 located between both the tapered portions 21, 23 and having a generally constant external diameter along the longitudinal direction; and a small-diameter portion 24 located on the distal end side of the second taper portion 23.

A portion of the wire main body 21 on the distal end side of the first tapered portion 21 is inserted through the generally central portion inside the coil 4. In the illustrated configuration, a portion of the wire main body 2 on the distal end side of the first tapered portion 21 is inserted through without contact with the inner surface of the coil 4. Incidentally, a portion of a proximal end side of the coil 4 may be in contact with the wire main body 2.

Examples of the metal material forming the wire main body 2 include stainless steel and a Ni—Ti alloy.

Because of having the first and second tapered portions 21, 23 the wire main body 2 can gradually be reduced in rigidity toward the distal end direction. This can improve insertion operability and also prevent bending.

Incidentally, although the wire main body 2 can be made of a single material such as stainless steel or a Ni—Ti alloy along its total length, it can be formed by combining different materials with each other.

In particular, preferably, the main body portion 20 (the proximal end side portion) is made of a relatively high-rigid material such as stainless steel. In addition, the distal end side of the main body portion 20, i.e., in the illustrated embodiment, the first tapered portion 21, the intermediate portion 22, the second tapered portion 23 and the small-diameter portion 24, is made of a material that has rigidity smaller than that of stainless steel such as a Ni—Ti alloy and exhibits wide elasticity such as superelasticity. In this way, while the guide wire 1 ensures satisfactory operability by obtaining superior indentation performance and torque transmissibility, its distal end side is improved in following performance for a blood vessel and safety by obtaining satisfactory flexibility and restoring performance.

Incidentally, the combination of the different materials in the wire main body 2 is not limited to the above. The different materials may appropriately be selected depending on its objective. For example, to improve shape-maintaining performance after reshaping, at least one of the intermediate portion 22, the second tapered portion 23 and the small-diameter portion 24 can be made of stainless steel. Although the main body portion 20 and the distal end side portion of the main body portion 20 are made of the same Ni—Ti alloy or the like, they may be different from each other in rigidity characteristic. Specifically, the main body portion 20 may have higher rigidity in view of material than the distal end side portion of the main body portion 20.

The shaping ribbon 3 is disposed at the distal end of the wire main body 2 so that a portion of its distal end side extends in the distal end direction from the distal end of the wire main body 2. The shaping ribbon 3 is disposed generally parallel to the wire main body 2. A portion of proximal end side is secured to the front surface of the second tapered portion 23 so as to overlap the small-diameter portion 24 of the wire main body 2. Incidentally, of the shaping ribbon 3, a portion located on the distal end side and projecting toward the distal end from the distal end of the wire main body 2 is called "the extending portion 31" and a portion located on the proximal end side and overlapping the wire main body 2 is called "the overlapping portion 32."

The reshaping (shaping) described above can be done easily and reliably by the presence of the shaping ribbon 3. Specifically, when the doctor or the like reshapes (shapes) the distal end portion of the guide wire 1 with her or his fingers, the shaping ribbon 3 is plastically deformed into a desired shape to exhibit a function of maintaining the shape. Incidentally, "reshapeable" means that the shaping ribbon 3 can be bent in a desired shape and the shape can be maintained.

The shaping ribbon 3 is secured to the wire main body 2 at the distal end and proximal end of the overlapping portion 32. Although the securing method is not restrictive, the shaping ribbon 3 is secured with a securing material 33 such as solder (brazing filler material), etc. in the present embodiment. As described above, the shaping ribbon 3 is secured to the wire main body 2 only at the two positions of the distal end and proximal end, not at the overall overlapping portion 32. Therefore, the mechanical characteristics of the overlapping portion 32 combine both the characteristic of the wire main body 2 and the characteristic of the shaping ribbon 3. Thus, if the wire main body 2 uses a wire material exhibiting superelasticity such as a Ni—Ti alloy, the mechanical characteristics of the overlapping portion 32 combine both the reshaping performance and superelasticity of the shaping ribbon 3. The guide wire 1 described above has such a mechanical characteristic as to gradually increase shaping performance as it goes toward the distal end direction, whereas to gradually increase superelasticity as it goes toward the proximal end direction. Such a guide wire 1 can easily be inserted into a blood vessel and is superior in branch selectability (superior in operability) at a branch portion of the blood vessel.

Other securing methods of securing the shaping ribbon 3 to the wire main body 2 include welding and adhesion with an adhesive.

In the shaping ribbon 3, the length of the extending portion 31 is preferably approximately 0.5 to 1 time, more preferably 0.7 to 0.9 time that of a portion (the overlapping portion 32) other than the extending portion 31. If the ratio of the extending portion 31 to the overlapping portion 32 is set to fall within the above-mentioned range, the guide wire 1 becomes particularly superior in the insertion performance into a blood vessel and in the branch selectability of a blood vessel.

The length of the extending portion 31 is preferably approximately 5 to 20 mm, more preferably approximately 10 to 15 mm. If the length of the extending portion 31 falls within the range, particularly operability is high. This provides the guide wire 1 with a high degree of safety.

The shaping ribbon 3 is made of a plastically deformable (reshapeable) material such as stainless steel. Therefore, the reshaping (shaping) described above can be done more easily and reliably.

Although not restrictive, under normal conditions the length of the shaping ribbon 3 is preferably approximately 0.5 to 4.0 cm, more preferably 1.5 to 3.0 cm. Since the shaping ribbon 3 is made of such a thin wire material, it has particularly high flexibility and easily becomes reshapeable.

As illustrated in a cross-sectional view taken along line A-A in FIG. 1, the shaping ribbon 3 is shaped like a flat plate or square column. The shaping ribbon 3 shaped rectangularly in section as mentioned above is more easily bent in the long side direction of the rectangle (the vertical direction in FIG. 1) than in the short side direction. Therefore, it has an advantage of easily managing the directionality of reshaping. In addition, although the shaping ribbon 3 shaped rectangularly in section has the same sectional area and almost the same degree of tension strength compared with that circular in section, it can ensure the flexibility in the long side direction so that following deformability encountered when stress is applied thereto can be improved.

Incidentally, the transverse sectional shape of the shaping ribbon 3 may be a quadrangle such as a square, a rectangle, a trapezoid.

The shaping ribbon 3 may partially have such a flat plate-like or prismatic column-like portion.

The shaping ribbon 3 may be such that its transverse sectional shape is uniform over the full length thereof or is partially varied (increased or decreased in area).

The shaping ribbon 3 may at least partially be provided with a layer of the radiopaque material described earlier. Thus, the small-diameter portion 24 can obtain radiographic visualization so that the guide wire 1 can be inserted into a living body while confirming the position of the distal end under radiographic guidance.

The coil 4 includes a helical first coil 41 installed at the distal end side of the wire main body 2 and a helical second coil 42 connected (joined) to the proximal end side of the first coil 41. The first coil 41 of them is located to cover the shaping ribbon 3 and the nearly overall small-diameter portion 24. The second coil 42 is located to cover the nearly overall intermediate portion 22.

The first coil 41 has a tight-pitch portion 411 in which a raw-wire is wound in a relatively tight manner, and a rough-pitch portion 412 in which the raw-wire is wound in a relatively rough manner. The tight-pitch portion 411 of them is formed at a position corresponding to the extending portion 31 of the shaping ribbon 3. On the other hand, the rough-pitch portion 412 is formed at a position corresponding to the above-mentioned overlapping portion 32.

Incidentally, the extending portion 31 located inside the tight-pitch portion 411 is composed of only the shaping ribbon 3; therefore, it has relatively low bending rigidity. On the other hand, the overlapping portion 32 is composed of the shaping ribbon 3 and the wire main body 2; therefore, it has a relatively high bending rigidity.

In the past, the guide wire having the wire main body and the shaping ribbon as described above has caused stress resulting from the difference in bending rigidity between them, in the vicinity of the joint portion between them. Since the stress locally concentrates on the joint portion so that the shaping ribbon bends at the joint portion, there arises a problem of impairing the function as the guide wire.

Consequently, in the present invention, the coil 4 provided to cover the shaping ribbon 3 and the distal end portion of the wire main body 2 is designed to have a function of eliminating the above-mentioned problem. Specifically, in the present embodiment, the tight-pitch portion 411 has higher bending rigidity of the coil per se than the rough-pitch portion 412. The difference in the bending rigidity of the coil 4 between them is used to alleviate the difference in bending rigidity between the extending portion 31 and the overlapping portion 32. This suppresses the local concentration of stress on the joint portion between the shaping ribbon 3 and the wire main body 2, which prevents the bending of the shaping ribbon 3. As a result, there is no possibility that the guide wire cannot be used because of bending, so that the guide wire 1 has a high degree of reliability.

The tight-pitch portion 411 is such that the raw-wire is helically formed and the helical parts are tightly arranged without gaps therebetween in the state where external force is not applied. The rough-pitch portion 412 is such that the raw-wire is helically formed and the helical parts are arranged to have gaps therebetween in the state where external force is not applied.

A difference between a pitch $P_1$ of the wire in the tight-pitch portion 411 and a pitch $P_2$ of the wire in the rough-pitch portion 412 is appropriately set according to a difference in bending rigidity between the extending portion 31 and the overlapping portion 32.

Specifically, it is preferred that the difference between the pitch $P_1$ and the pitch $P_2$ be set so that the difference of bending rigidity of the coil 4 per se resulting from the difference between the pitches complements the difference in bending rigidity between the extending portion 31 and the overlapping portion 32. This more reliably suppresses the concentration of the stress occurring at the above-mentioned joint portion, so that the bending of the shaping ribbon 3 can be prevented reliably.

Incidentally, the pitch $P_1$ of the raw-wire in the tight-pitch portion 411 and the pitch $P_2$ of the raw-wire in the rough-pitch portion 412 each correspond to a distance between the centers of the adjacent raw-wires as shown in FIG. 1.

The difference between the pitch $P_1$ of the tight-pitch portion 411 and the pitch $P_2$ of the rough-pitch portion 412 is set as described above. More specifically, it is preferred that the following condition be satisfied.

The condition is as below. It may be assumed that the bending rigidity of the overall guide wire 1 at a portion corresponding to the extending portion 31 is X and the bending rigidity of the overall guide wire 1 at a portion corresponding to the overlapping portion 32 is Y. In such a case, the relationship in which X/Y is preferably approximate 0.7 to 1, more preferably approximate 0.8 to 1 is satisfied. If such a condition is satisfied, the guide wire 1 has entirely uniform bending rigidity and slightly flexible at the distal end side. Thus, the guide wire 1 can easily be inserted into a blood vessel and has a high degree of operability.

In the present embodiment described above, the difference between the pitch $P_1$ of the tight-pitch portion 411 and the pitch $P_2$ of the rough-pitch portion 412 is appropriately set only. This can easily alleviate the difference in bending rigidity between the distal end side portion and proximal end side portion of the guide wire 1, and thus the reliability of the guide wire 1 can be enhanced.

The second coil 42 is fixedly connected to the distal end side of the first coil 41. Although the arrangement and the securing method for both the coils are not restrictive, the proximal portion of the first coil 41 and the distal portion of the second coil 42 are arranged to confront each other in the embodiment.

Also the second coil 42 is obtained by helically forming a raw-wire, in which the helical parts are tightly arranged without gaps therebetween in the state where external force is not applied.

Examples of metal materials forming the first coil 41 and the second coil 42 as described above include a superelastic alloy such as stainless steel or a Ni—Ti alloy, a shape-memory alloy, a cobalt-based alloy, noble metal such as gold or platinum, and a tungsten-based alloy. In particular, by use of a radiopaque material such as noble metal or a tungsten-based alloy, the guide wire 1 can provide radiographic visualization. Thus, preferably, while confirming the position of the distal end under radiographic guidance, the guide wire can be inserted into a living body.

Incidentally, in the present embodiment, the first coil 41 and the second coil 42 each use a raw-wire circular in section. However, the invention is not limited to this. The section of the raw-wire may be e.g. an ellipse or a quadrangle (particularly, a rectangle).

In the present embodiment, the first coil 41 and the second coil 42 are different from each other in the diameter of the raw-wire forming each of them, and thus also in helical pitch; however, they may be the same.

Further, the first coil 41 and the second coil 42 may be different from each other in conditions such as a material and sectional shape of the raw-wire, the outer diameter and inner diameter of the coil, etc.

In the present embodiment, the coil 4 is divided into the first coil 41 and the second coil 42. However, the coil 4 may be a single piece.

The second coil 42 is secured at the proximal portion to the proximal end side of the intermediate portion 22 of the wire main body 2. This securing method is not particularly restrictive. However, in the present embodiment, the second coil 42 is secured by a securing material 51 such as solder (brazing filler metal). Incidentally, other securing methods include welding and adhesion by an adhesive.

A connecting portion (a joint portion) between the first coil 41 and the second coil 42 is secured to the second tapered portion 23 of the wire main body 2. This securing method is not particularly restrictive. However, in the present embodiment, the connecting portion is secured by a securing member 52 such as solder (brazing filler metal).

Further, the first coil 41 is secured at the distal portion to the distal end side of the shaping ribbon 3. Also this securing method is not restrictive. However, in the present embodiment, the first coil 41 is secured by a securing member 53 such as solder (brazing filler metal).

Incidentally, the securing by use of the securing material 52, 53 may be replaced with the securing method such as welding, adhesion by an adhesive or the like.

Preferably, the proximal end surface of the securing member 51 and the distal end surface of the securing member 53 are preferably rounded to prevent the inner wall of a blood vessel from being damaged.

Preferably, the front surface (particularly the external surface) of the coil 4 (the first coil 41 and the second coil 42) is wholly or partially covered with a film (not illustrated) made of hydrophilic material or hydrophobic material. This can make the insertion of the guide wire 1 smoother.

Such a film includes various modes depending on objectives. Its examples include a mode in which the respective entire external surfaces of the first coil 41 and the second coil 42 are covered with a lubricative hydrophobic film; a mode in which only a distal end side, of the first coil 41, with a predetermined length is covered with a lubricative hydrophobic film and the other portion of the first coil 41 and the second coil 42 is covered with a hydrophilic film; and a mode in which the film is not present on the distal end side, of the first coil 41, with a predetermined length and the other portion of the first coil 41 and the second coil 42 are covered with a hydrophilic or hydrophobic film.

Examples of hydrophilic material forming the film include cellulosic high-molecular material, polyethylene oxide-based high-molecular material, maleic acid anhydride-based high-molecular material (maleic anhydride copolymer such as e.g. methyl vinyl ether/maleic anhydride copolymer), acryl amide-based high-molecular material (e.g. polyacrylamide, block copolymer of polyglycidylmethacrylate-dimethylacrylamide (PGMA-DMAA)), hydrosoluble nylon, and polyvinyl alcohol.

Examples of hydrophobic material forming the film include a fluorinated resin such as polytetrafluoroethylene, and silicon series material.

Second Embodiment

Figure 2:
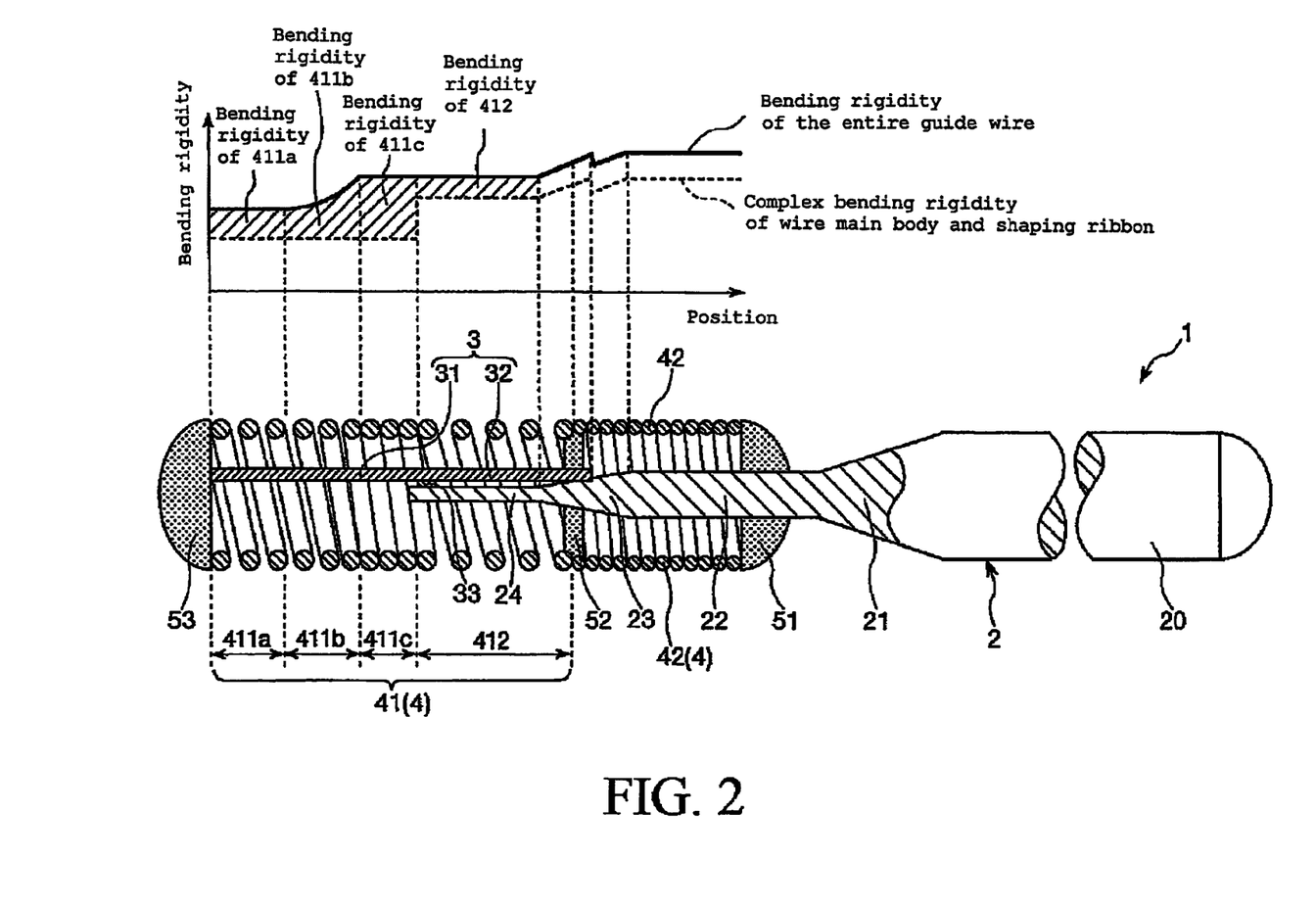
FIG. 2 is a longitudinal cross-sectional view illustrating a second embodiment of a guide wire of the present invention.

FIG. 2 includes a longitudinal cross-sectional view illustrating a second embodiment of the guide wire of the present invention and a graph schematically illustrating bending rigidity of each portion. It is to be noted that the right and left of FIG. 2 are referred to as "the proximal end" and "the distal end," respectively, for explanatory convenience. In addition, for easy understanding, FIG. 2 schematically illustrates the guide wire shortened in longitudinal length and exaggerated in diameter so that the ratio between the longitudinal length and the diameter is largely different from that between the actual ones.

The second embodiment of the guide wire of the present invention will hereinafter be described with reference to FIG. 2. However, the description is given focusing on points different from the embodiment described above and the explanation of the same matters is omitted.

The present embodiment is the same as the first embodiment except that a configuration of a first coil 41 is different from that of the first embodiment.

The guide wire 1 illustrated in FIG. 2 includes a wire main body 2, a shaping ribbon (wire) 3, and a coil 4 having an area in which the pitches of a raw-wire are different from each other.

The coil 4 illustrated in FIG. 2 includes a first coil 41 and a second coil 42. The first coil 41 of them has an area where the raw-wire is wound relatively tightly and an area (a rough-pitch portion 412) which is located on the proximal end side of the former area and in which the raw-wire is wound relatively roughly. The area where the raw-wire is wound relatively tightly is formed at a portion corresponding to an extending portion 31 of the shaping ribbon 3. On the other hand, the area (the rough-pitch portion 412) where the raw-wire is wound relatively roughly is formed at a portion corresponding to the overlapping portion 32 described earlier. Thus, the bending rigidity of the area where the raw-wire is wound relatively tightly is higher than that of the area (the rough-pitch portion 412) where the raw-wire is wound relatively roughly.

In this case, the area where the raw-wire is wound relatively tightly is divided into three areas, an area 411*a*, an area 411*b* and an area 411*c* rowed in this order from the distal end side.

Of them, in the area 411*c* located on the most proximal end side, the raw-wire is tightly wound so as not to produce gaps between the raw-wires. Therefore, the bending rigidity of the area 411*c* is relatively high.

On the other hand, in the area 411*a* located on the most distal end side, the raw-wire is wound to produce gaps between the raw-wires. Therefore, the bending rigidity of the area 411*a* is relatively low compared with that of the area 411*c*.

In the area 411*b* located between the area 411*a* and the area 411*c*, the pitch of the raw-wire is gradually increased as it goes toward the area 411*a* from the area 411*c* (toward the distal end side from the proximal end side). In other words, the pitch of the raw-wire in the area 411*b* is varied to smoothly connect the pitch of the raw-wire in the area 411*c* with the pitch of the raw-wire in the area 411*a*. Thus, the bending rigidity of the area 411*b* is gradually reduced toward the distal end side from the proximal end side.

Incidentally, the bending rigidity of the extending portion 31 is lower than that of the overlapping portion 32 similarly to the first embodiment. The magnitude relation of the bending rigidity is illustrated as e.g. a graph of a broken line (the complex bending rigidity of the wire body 2 and the shaping ribbon 3) in FIG. 2.

On the other hand, the bending rigidity of the entire guide wire 1 is illustrated as e.g. a graph of a solid line in FIG. 2. The bending rigidity of the entire guide wire 1 is the complex bending rigidity of the wire main body 2, the shaping ribbon 3 and the coil 4.

Thus, the bending rigidity of the first coil 41 is obtained by subtracting the complex bending rigidity of the wire main body 2 and the shaping ribbon 3 from the bending rigidity of the entire guide wire 1. The bending rigidity of the first coil 41 is illustrated as a hatched area of the graph of FIG. 2.

As seen from the graph of FIG. 2, a portion of the coil 4 corresponding to an extending portion 31 has a portion where the bending rigidity of the coil 4 is gradually reduced as it goes toward the distal direction. Therefore, also the bending rigidity of the entire guide wire 1 is reduced as it goes toward the distal direction without abrupt rigidity-difference.

In the guide wire 1 described above, first, the difference in bending rigidity between the extending portion 31 and the overlapping portion 32 is alleviated by the difference in bending rigidity between the area 411c and the rough-pitch portion 412. This suppresses the local concentration of stress on the joint portion between the shaping ribbon 3 and the wire main body 2. Therefore, the shaping ribbon 3 is prevented from being bent. Consequently, there is no possibility that the guide wire 1 cannot be used because of bending, so that the guide wire 1 has a high degree of reliability.

The guide wire 1 is gradually reduced in bending rigidity as it goes toward the area 411a from the area 411c; therefore, the most distal portion has high flexibility. Thus, when the guide wire 1 is inserted into a blood vessel, insertion operation can safely be done without any damage to a blood vessel wall. As an alternative, the raw-wire of the coil in the area 411a and the area 411b can be reduced in diameter. Also in this case, the pitch of the raw-wire in the area 411b is gradually increased as it goes toward the area 411a from the area 411c (toward the distal end side from the proximal end side). Therefore, particularly the flexibility of the most distal portion can be made high.

As described above, in the present embodiment, only the winding number, per unit length, of the core-wire of the coil 4 is simply set. This can easily alleviate the difference in bending rigidity between the distal portion and proximal portion of the guide wire 1. Thus, the reliability of the guide wire 1 can be enhanced.

Third Embodiment

Figure 3:
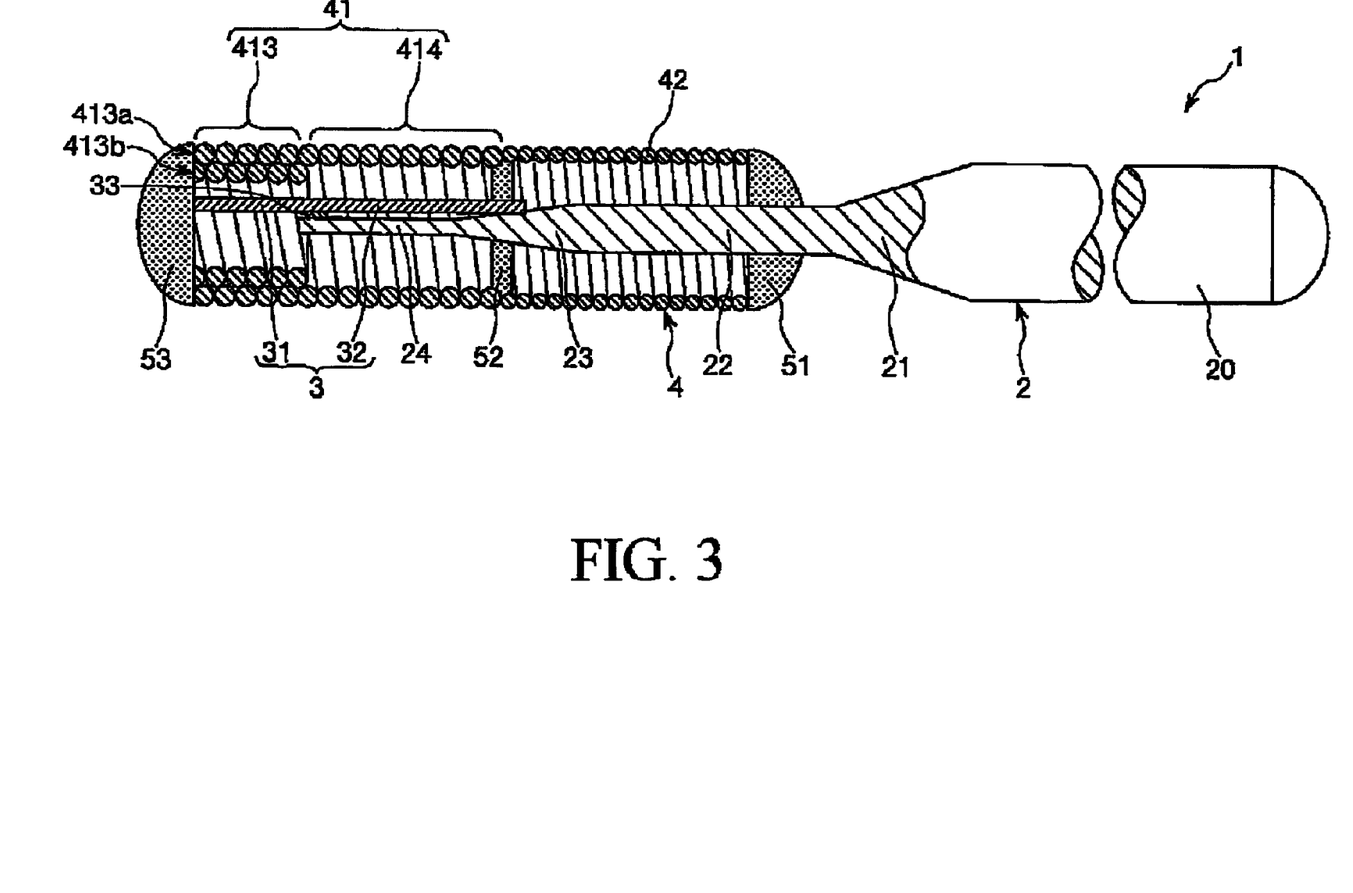
FIG. 3 is a longitudinal cross-sectional view illustrating a third embodiment of a guide wire of the present invention.

FIG. 3 is a longitudinal cross-sectional view illustrating a third embodiment of the guide wire of the present invention. It is to be noted that the right and left of FIG. 3 are referred to as "the proximal end" and "the distal end," respectively, for explanatory convenience. In addition, for easy understanding, FIG. 3 schematically illustrates the guide wire shortened in longitudinal length and exaggerated in diameter so that the ratio between the longitudinal length and the diameter is largely different from that between the actual ones.

The third embodiment of the guide wire of the present invention will hereinafter be described with reference to FIG. 3. However, the description is given focusing on points different from the embodiments described above and the explanation of the same matters is omitted.

The present embodiment is the same as the first embodiment except that a configuration of a first coil 41 is different from that of the first embodiment.

The guide wire 1 illustrated in FIG. 3 includes a wire main body 2, a shaping ribbon (wire material) 3 and a coil 4 in which a portion on the distal end side has dual helixes.

The coil 4 illustrated in FIG. 3 includes the first coil 41 and a second coil 42. The first coil 41 of them has a double-helix portion 413 where a raw-wire is doubly wound and a single-helix portion where the raw-wire is singly wound. The double-helix portion 413 is formed at a portion corresponding to an extending portion 31 of the shaping ribbon 3. On the other hand, the single-helix portion 414 is formed at a position corresponding to an overlapping portion 32 where the shaping ribbon 3 and the wire main body 2 overlap each other. Incidentally, the double-helix portion 413 and the single-helix portion 414 are formed to have almost the same pitch of the raw-wire.

Similarly to the first embodiment, the extending portion 31 is composed of only the shaping ribbon 3; therefore, it has relatively lower bending rigidity than the overlapping portion 32.

On the other hand, the double-helix portion 413 is increased in the bending rigidity of the coil per se because it has the higher winding number of the raw-wire per unit length than that of the single-helix portion 414. Therefore, the difference of the bending rigidity of the coil is used to alleviate the difference in the bending rigidity between the extending portion 31 and the overlapping portion 32 described above. This suppresses the local concentration of stress on the joint portion between the shaping ribbon 3 and the wire main body 2. Therefore, the shaping ribbon 3 can be prevented from being bent. Consequently, there is no possibility that the guide wire 1 becomes hard to use because of bending, so that it has high operability.

The double-helix portion 413 is composed of an external helix portion 413a located on the outside and an internal helix portion 413b located on the inside. The internal helix portion 413b terminates at the distal end of the overlapping portion 32, i.e., at the proximal end of the extending portion 31. Therefore, the difference in bending rigidity between the extending portion 31 and the overlapping portion 32 is alleviated.

In the present embodiment, both the external helical portion 413a and the internal helical portion 413b are such that the raw-wire is tightly wound; however, both or one of them may have gaps between the raw-wires.

In the present embodiment, the raw-wire is doubly wound in the double-helix portion 413 and is singly wound in the single-helix portion 414. The combination of the winding number of the raw-wire is not limited to this. The winding number of the raw-wire in the double-helix portion 413 needs only to be higher than that in the single-helix portion 414. For example, the raw-wire may triply be wound in the double-helix portion 413 and may doubly be wound in the single-helix portion 414. Similarly to the second embodiment, if the extending portion 31 is divided into the three areas 411a, 411b and 411c as in FIG. 2, the areas 411a, 411b may be a single-helix portion and the area 411c may be a double-helix portion. Alternatively, the areas 411a, 411b and 411c may be a single-helix portion, a double-helix portion and a triple-helix portion, respectively.

Incidentally, a difference in the winding number of the raw-wire per unit length between the double-helix portion 413 and the single-helix portion 414 are appropriately set depending on the difference in bending rigidity between the extending portion 31 and the overlapping portion 32.

Specifically, it is preferred that the difference in the winding number of the raw-wire per unit length between the double-helix portion 413 and the single-helix portion 414 be set so that the difference of the bending rigidity of the coil 4 per se due to the difference of the winding number complements the difference in bending rigidity between the extending portion 31 and the overlapping portion 32. This more reliably suppresses the concentration of stress occurring at the joint portion mentioned above. Thus, the bending of the shaping ribbon 3 can reliably be prevented.

In the present embodiment described above, by just appropriately setting the winding number of the raw-wire per unit length in the coil 4, the difference in bending rigidity between the distal end side portion and proximal end side portion of the guide wire 1 can easily be alleviated and thus the reliability of the guide wire 1 can be enhanced.

Fourth Embodiment

Figure 4:
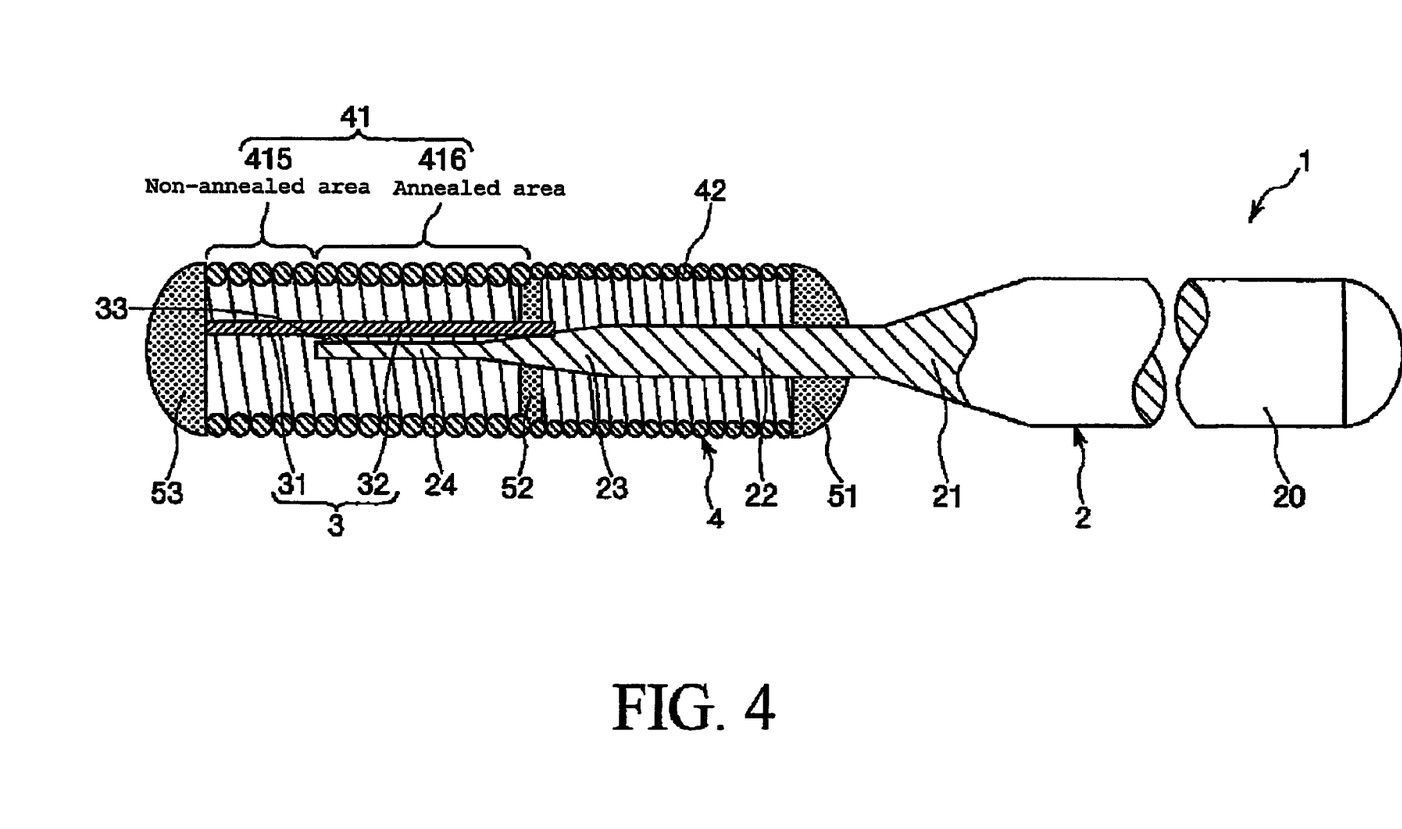
FIG. 4 is a longitudinal cross-sectional view illustrating a fourth embodiment of a guide wire of the present invention.

FIG. 4 is a longitudinal cross-sectional view illustrating a fourth embodiment of the guide wire of the present invention. It is to be noted that the right and left of FIG. 4 are referred to as "the proximal end" and "the distal end," respectively, for explanatory convenience. In addition, for easy understanding, FIG. 4 schematically illustrates the guide wire shortened in longitudinal length and exaggerated in diameter so that the ratio between the longitudinal length and the diameter is largely different from that between the actual ones.

The fourth embodiment of the guide wire of the present invention will hereinafter be described with reference to FIG. 4. However, the description is given focusing on points different from the embodiments described above and the explanation of the same matters is omitted.

The present embodiment is the same as the first embodiment except that a configuration of a first coil 41 is different from that of the first embodiment.

A guide wire 1 illustrated in FIG. 4 includes a wire main body 2, a shaping ribbon (wire material) 3 and a coil 4 subjected to partial annealing.

In the coil 4 illustrated in FIG. 4, a portion corresponding to an overlapping portion 32 is subjected to partial annealing. The portion subjected to the annealing is hereinafter called the annealed area 416. On the other hand, a portion corresponding to an extending portion 31 of the coil 4 is not subjected to annealing. This area is hereinafter called the non-annealed area 415.

Annealing is heat treatment in which a metal material is heated to an appropriate temperature and thereafter gradually cooled. In general, hardening and stress resulting from the processing remain in the metal material. If such a metal material is subjected to annealing, the metal structure is reduced in lattice defect and homogenized. Therefore, the processing hardening and residual stress mentioned above are reduced, with the result that the metal material is softened by the annealing.

Because of this, the annealed area 416 located on the proximal end side of the coil 4 is lower in the hardness of a raw-wire per se of the coil 4 than the non-annealed area 415 located on the distal end side. Therefore, the annealed area 416 is relatively lower in the bending rigidity of the coil per se than the non-annealed area 415. In other words, the non-annealed area 415 is relatively higher in the bending rigidity of the coil per se than the annealed area 416.

Incidentally, similarly to the first embodiment, the extending portion 31 is relatively lower in bending rigidity than the overlapping portion 32.

From this view point, the present embodiment uses the difference of the bending rigidity provided in the coil 4 to alleviate the difference in bending rigidity between the extending portion 31 and the overlapping portion 32 described above. This suppresses the local concentration of stress on the joint portion between the shaping ribbon 3 and the wire main body 2. Thus, the shaping ribbon 3 can be prevented from being bent. Consequently, there is no possibility that the guide wire 1 cannot be used because of bending, so that the guide wire 1 has a high degree of reliability.

Incidentally, the conditions of annealing applied to the annealed area 416 are appropriately set depending on the difference in bending rigidity between the extending portion 31 and the overlapping portion 32.

Specifically, it is preferred that the conditions of the annealing applied to the annealed area 416 be set so that a difference in the hardness of the raw-wire per se between the annealed area 416 and the non-annealed area 415 resulting from the annealing and a difference in the bending rigidity of the coil per se resulting from the difference in the hardness complement the difference in bending rigidity between the extending portion 31 and the overlapping portion 32. This more reliably suppresses the concentration of stress occurring in the joint portion described above. Thus, the shaping ribbon 3 can reliably be prevented from being bent.

In the present embodiment described above, by simply subjecting a portion of the coil 4 to annealing, the difference in bending rigidity between the distal end side portion and proximal end side portion of the guide wire 1 can easily alleviated. Thus, the reliability of the guide wire 1 can be enhanced.

Fifth Embodiment

Figure 5:
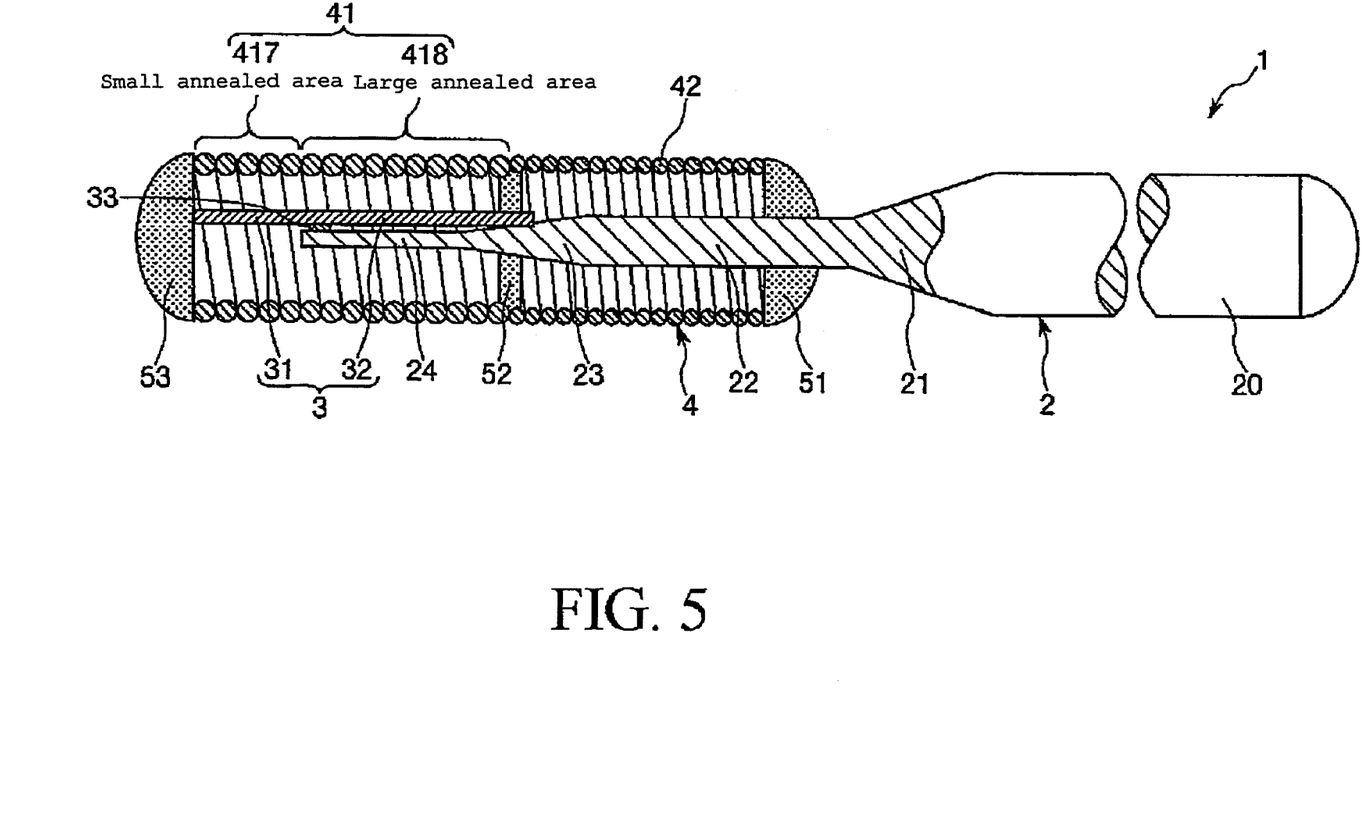
FIG. 5 is a longitudinal cross-sectional view illustrating a fifth embodiment of a guide wire of the present invention.

FIG. 5 is a longitudinal cross-sectional view illustrating a fifth embodiment of the guide wire of the present invention. It is to be noted that the right and left of FIG. 5 are referred to as "the proximal end" and "the distal end," respectively, for explanatory convenience. In addition, for easy understanding, FIG. 5 schematically illustrates the guide wire shortened in longitudinal length and exaggerated in diameter so that the ratio between the longitudinal length and the diameter is largely different from that between the actual ones.

The fifth embodiment of the guide wire of the present invention will hereinafter be described with reference to FIG. 5. However, the description is given focusing on points different from the embodiments described above and the explanation of the same matters is omitted.

The present embodiment is the same as the first embodiment except that a configuration of a first coil 41 is different from that of the first embodiment.

A guide wire 1 illustrated in FIG. 5 includes a wire main body 2, a shaping ribbon (wire material) 3 and a coil 4 subjected to annealing.

The coil 4 illustrated in FIG. 5 is subjected to annealing so that an annealing amount resulting from annealing applied to a portion corresponding to an overlapping portion 32 is greater than that corresponding to an extending portion 31. Hereinafter, the portion corresponding to the overlapping portion 32 of the coil 4 is referred to as the large annealed area 418 and the portion corresponding to the extending portion 31 is referred to as the small annealed area 417.

Here, the annealing amount implies the degree of annealing of the coil 4 resulting from the annealing. For example, annealing may be performed by heating on the small annealed area 417 and the large annealed area 418 in the same method. In such a case, a difference between the annealing amounts mentioned above occurs due to the difference in the respective heat quantities applied to the small annealed area 417 and the large annealed area 418. Specifically, the large annealed area 418 is heated at higher temperature or for a longer period of time than the small annealed area 418. This can provide a difference between respective heat quantities applied to the small annealed area 417 and the large annealed area 418.

The annealing condition is made different between the small annealed area 417 and the large annealed area 418 as described above. This makes the small annealed area 417 higher in the hardness of the raw-wire per se of the coil 4 than the large annealed area 418. Thus, the small annealed area 417 is relatively increased in the bending rigidity of the coil per se than the large annealed area 418.

From this view point, similarly to the third embodiment, the present embodiment uses the difference of the bending rigidity provided in the coil 4 to alleviate the difference in bending rigidity between the extending portion 31 and the overlapping portion 32 described above. This suppresses the local concentration of stress on the joint portion between the shaping ribbon 3 and the wire main body 2. Thus, the shaping ribbon 3 can be prevented from being bent. Consequently, there is no possibility that the guide wire 1 cannot be used because of bending, so that the guide wire 1 has a high degree of reliability.

Incidentally, the respective conditions of annealing applied to the small annealed area 417 and the large annealed area 418 are appropriately set depending on the difference in bending rigidity between the extending portion 31 and the overlapping portion 32.

Specifically, it is preferred that the conditions of the annealing applied to each of the small annealed area 417 and the large annealed area 418 be set so that a difference in the hardness of the raw-wire per se between the small annealed area 417 and the large annealed area 418 resulting from the annealing and a difference in the bending rigidity of the coil per se resulting from the difference in the hardness complement the difference in bending rigidity between the extending portion 31 and the overlapping portion 32. This more reliably suppresses the concentration of stress occurring in the joint portion described above. Thus, the shaping ribbon 3 can reliably be prevented from being bent.

In the present embodiment described above, by just partially varying the annealing applied to the coil 4, the difference in bending rigidity between the distal end side portion and proximal end side portion of the guide wire 1 can easily be alleviated and thus the reliability of the guide wire 1 can be enhanced.

The guide wire of the present invention has been described thus far with reference to the illustrated embodiments. However, the present invention is not limited to these. The parts constituting the guide wire can be replaced with arbitrarily configured parts exhibiting the same functions. An arbitrary constitutional part may be added to each of the embodiments.

The guide wire of the present invention may be a combination of arbitrary two or more constitutional elements of those of the embodiments described above.

Examples of methods of making bending rigidity different between the distal end side portion and proximal end side portion of the coil include a method of enhancing bending rigidity by partially welding (e.g. laser welding, electron beam welding) between the raw-wires of the coil; and a method of partially forming a reinforcing layer reinforcing a coil, on the front surface of the coil.

INDUSTRIAL APPLICABILITY

The guide wire of the present invention includes a wire main body having flexibility; a reshapeable wire material having a portion, on a proximal end side, secured to a distal end side of the wire main body, and an extending portion, at a portion on a distal end side, extending in a distal direction from a distal end of the wire main body; and a coil installed to cover the distal end side of the wire main body and the wire material, the coil obtained by helically forming a raw-wire; and is characterized in that in the coil, bending rigidity of the coil per se of a distal end side portion located at a position corresponding to the extending portion is higher than that of a proximal end side portion located at a position closer to the proximal end side than to the distal end side portion. Therefore, the difference in the bending rigidity of the coil per se is used to suppress the local concentration of stress on the joint portion between the wire material and the wire main body. Thus, the wire material can be prevented from being bent. Consequently, there is no possibility that the guide wire cannot be used because of being bent, and the guide wire has high reliability, combining both excellent reshaping performance and operability. If the wire material exhibiting superelasticity is used as the wire main body, the guide wire has such a mechanical characteristic as to become dominant in the reshapeable characteristic of the wire material to increase reshaping performance as it goes in the distal direction. In contrast, the guide wire becomes dominant in the characteristic of the wire main body to increase superelasticity as it goes in the proximal direction. The bending rigidity of the distal end side portion of the coil is made to be gradually reduced from the proximal end toward the distal end. In particular, this can increase flexibility at the most distal portion of the guide wire. Therefore, when such a guide wire is inserted into a blood vessel, insertion operation can be done safely without any damage to the wall of the blood vessel. Thus, the guide wire of the present invention has industrial applicability.

The invention claimed is:

1. A guide wire comprising:
a wire main body having flexibility;
a reshapeable wire material separate and distinct from said wire main body and having a portion, on a proximal end side, secured to a distal end side of the wire main body and overlapping a portion of the wire main body, and an extending portion, at a portion on a distal end side, extending in a distal end direction from the distal end side of the wire main body; and
a coil installed to cover the distal end side of the wire man body and the wire material, the coil being obtained by helically forming a raw-wire;
wherein a bending rigidity of the coil per se of a distal end side portion located at a position corresponding to the extending portion is higher than a bending rigidity of the coil per se of a proximal end side portion located at a position corresponding to the portion overlapping the portion of the wire main body and closer to the proximal end side than the distal end side portion;
wherein the guide wire in the extending portion has a first area, a second area, and a third area; the first area is located distally of the third area and the second area is located between the first area and the third area, a bending rigidity of the entire guide wire at the third area is higher than a bending rigidity of the entire guide wire at the first area, and a bending rigidity of the entire guide wire at the second area is gradually reduced toward the distal end side from the proximal end side; and
wherein the extending portion extends parallel to a longitudinal axis of the wire main body.

2. The guide wire according to claim 1, wherein a difference in the bending rigidity of the coil results from a difference in a pitch of the raw-wire, between the distal end side portion and the proximal end side portion.

3. The guide wire according to claim 1, wherein the distal end side portion of the coil is obtained by multi-helically forming the raw-wire and the proximal end side portion of the coil is obtained by single- or multi-helically forming the raw-wire; and wherein a difference in the bending rigidity of the coil results from a difference in the overlapping number of the raw-wire between the distal end side portion and the proximal end side portion.

4. The guide wire according to claim 1, wherein a difference in the bending rigidity of the coil results from a difference in hardness of the raw wire per se between the distal end side portion and the proximal end side portion.

5. The guide wire according to claim 4, wherein a difference in hardness of the raw-wire per se results from a difference in condition of annealing applied to the raw-wire between the distal end side portion and the proximal end side portion.

6. The guide wire according to claim 1, wherein the bending rigidity of the coil per se in the distal end side portion is partially gradually reduced from the proximal end side toward the distal end side.

7. The guide wire according to claim 1, wherein a bending rigidity of the extending portion located within the distal end side portion of the coil is lower than a bending rigidity of an overlapping portion located within the proximal end side portion of the coil, the overlapping portion including the portion of the reshapeable wire material overlapping the portion of the wire main body and the portion of the wire main body.

8. The guide wire according to claim 7, wherein the bending rigidity of the distal end side portion of the coil and the bending rigidity of the proximal end side portion of the coil are predetermined so as to compensate for the difference in the bending rigidity between the extending portion and the overlapping portion.

9. A guide wire comprising:
a wire main body having flexibility;
a reshapeable wire material separate and distinct from said wire main body and having a portion, on a proximal end side, secured to a distal end side of the wire main body and overlapping a portion of the wire main body, and an extending portion, at a portion on a distal end side, extending in a distal end direction from the distal end side of the wire main body; and
a coil installed to cover the distal end side of the wire man body and the wire material, the coil being obtained by helically forming a raw-wire;
wherein a bending rigidity of the coil per se of a distal end side portion located at a position corresponding to the extending portion is higher than a bending rigidity of the coil per se of a proximal end side portion located at a position corresponding to the portion overlapping the portion of the wire main body and closer to the proximal end side than the distal end side portion;
wherein the guide wire in the extending portion has a first area, a second area, and a third area; the first area is located distally of the third area and the second area is located between the first area and the third area, a bending rigidity of the entire guide wire at the third area is higher than a bending rigidity of the entire guide wire at the first area, and a bending rigidity of the entire guide wire at the second area is gradually reduced toward the distal end side from the proximal end side; and
wherein a pitch of the helically formed coil is varied over a length of the extending portion so as to thereby define the first area, the second area, and the third area.

10. The guide wire according to claim 9, wherein a difference in the bending rigidity of the coil results from a difference in the pitch between the distal end side portion and the proximal end side portion.

11. The guide wire according to claim 9, wherein the distal end side portion of the coil is obtained by multi-helically forming the raw-wire and the proximal end side portion of the coil is obtained by single- or multi-helically forming the raw-wire; and wherein a difference in the bending rigidity of the coil results from a difference in the overlapping number of the raw-wire between the distal end side portion and the proximal end side portion.

12. The guide wire according to claim 9, wherein a difference in the bending rigidity of the coil also results from a difference in hardness of the raw wire per se between the distal end side portion and the proximal end side portion.

13. The guide wire according to claim 12, wherein a difference in hardness of the raw-wire per se results from a difference in condition of annealing applied to the raw-wire between the distal end side portion and the proximal end side portion.

14. The guide wire according to claim 9, wherein the bending rigidity of the coil per se in the distal end side portion is partially gradually reduced from the proximal end side toward the distal end side.

15. The guide wire according to claim 9, wherein a bending rigidity of the extending portion located within the distal end side portion of the coil is lower than a bending rigidity of an overlapping portion located within the proximal end side portion of the coil, the overlapping portion including the portion of the reshapeable wire material overlapping the portion of the wire main body and the portion of the wire main body.

16. The guide wire according to claim 15, wherein the bending rigidity of the distal end side portion of the coil and the bending rigidity of the proximal end side portion of the coil are predetermined so as to compensate for the difference in the bending rigidity between the extending portion and the overlapping portion.

* * * * *